United States Patent [19]

O'Neil

[11] Patent Number: 5,364,377
[45] Date of Patent: Nov. 15, 1994

[54] FLUID COUPLING AND THE METHOD OF MANUFACTURE

[76] Inventor: Alexander G. B. O'Neil, 102 Lawler Street, Subiaco 6008, Perth, Australia

[21] Appl. No.: 910,312
[22] PCT Filed: Dec. 21, 1990
[86] PCT No.: PCT/GB90/02012
 § 371 Date: Sep. 2, 1992
 § 102(e) Date: Sep. 2, 1992
[87] PCT Pub. No.: WO91/10861
 PCT Pub. Date: Jul. 25, 1991

[30] Foreign Application Priority Data

Jan. 18, 1990 [AU] Australia .................. PJ8242
Jun. 29, 1990 [AU] Australia .................. PK0893
Aug. 30, 1990 [AU] Australia .................. PK2021

[51] Int. Cl.$^5$ ............................. A61M 25/00
[52] U.S. Cl. ................... 604/283; 604/284; 604/905; 285/137.1; 156/296; 156/294
[58] Field of Search .......... 604/246, 257, 258, 283, 604/284, 905; 285/25, 30, 131, 137.1, 260, 383, 422, 425; 156/73.2, 294, 296

[56] References Cited

U.S. PATENT DOCUMENTS

| | | | |
|---|---|---|---|
| 3,506,130 | 4/1970 | Shaye | 604/252 |
| 3,782,382 | 1/1974 | Naffulin et al. | |
| 3,999,284 | 12/1976 | Bicher | 29/570 |
| 4,072,146 | 2/1978 | Howes | |
| 4,257,416 | 3/1981 | Prager | |
| 4,585,435 | 4/1986 | Vaillancourt | 604/27 |
| 4,615,115 | 10/1986 | Bosshard et al. | 29/860 |
| 4,838,881 | 6/1989 | Bennett | 604/280 |
| 4,994,048 | 2/1991 | Metzger | 604/283 |
| 5,228,338 | 7/1993 | Saghatchi | 73/201 |

FOREIGN PATENT DOCUMENTS

| | | |
|---|---|---|
| 8903866 | 3/1989 | European Pat. Off. |
| 0360471 | 9/1989 | European Pat. Off. |
| 8118162 | 9/1981 | France |
| 8510919 | 4/1985 | Germany |
| 1297746 | 5/1947 | United Kingdom |
| 8802039 | 6/1988 | WIPO |

*Primary Examiner*—John D. Yasko
*Assistant Examiner*—Corrine Maglione
*Attorney, Agent, or Firm*—Ratner & Prestia

[57] ABSTRACT

A fluid coupling for connecting a plurality of fluid sources to a single-bore outlet member, said coupling comprising a plurality of tubes (44, 46, 48) mutually conjoined within a connector (42) for attachment of said outlet member, each said tube extending through said connector to terminate at a point (43) which is substantially contiguous with said outlet member when attached to said connector, the lumens of each said tube being mutually isolated by the tube walls until the termination of the tubes at said point, whereby in use of said fluid coupling with said single-bore outlet member connected thereto, fluid passing down any of said tubes discharges from the end of the respective tube substantially directly into the bore of said outlet member.

3 Claims, 5 Drawing Sheets

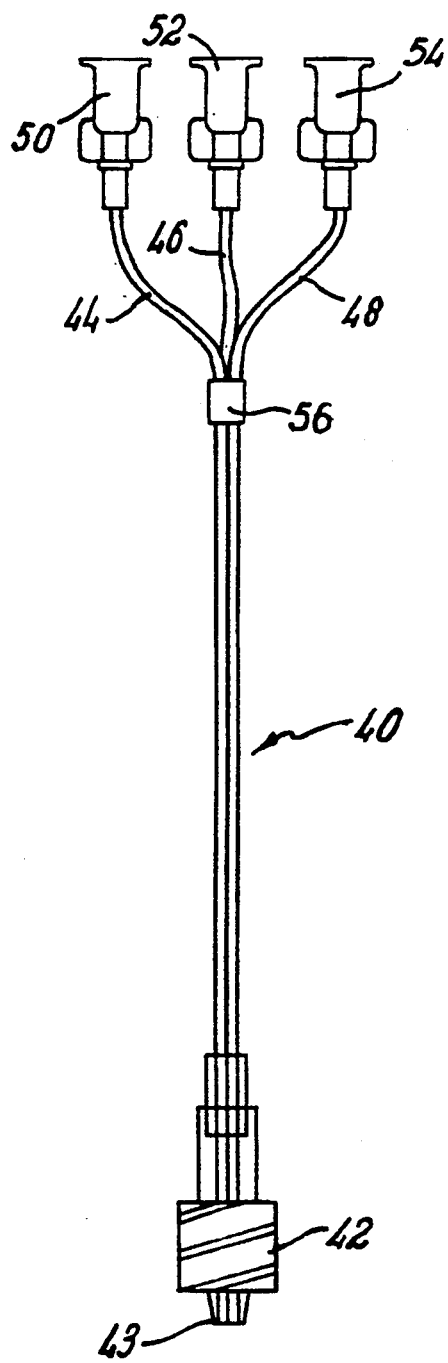
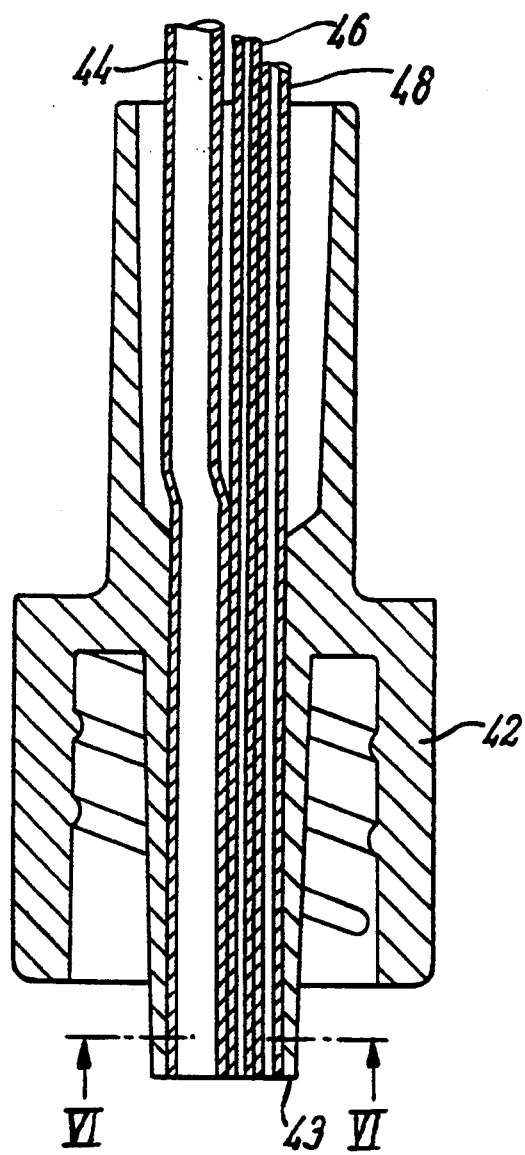
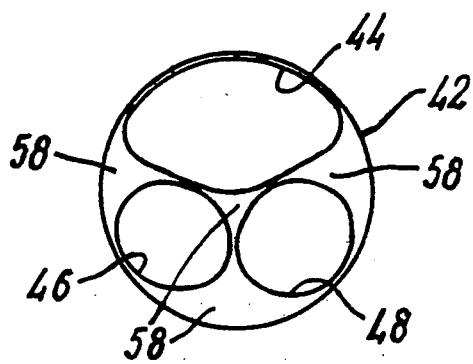
Fig. 4
Fig. 5
Fig. 6

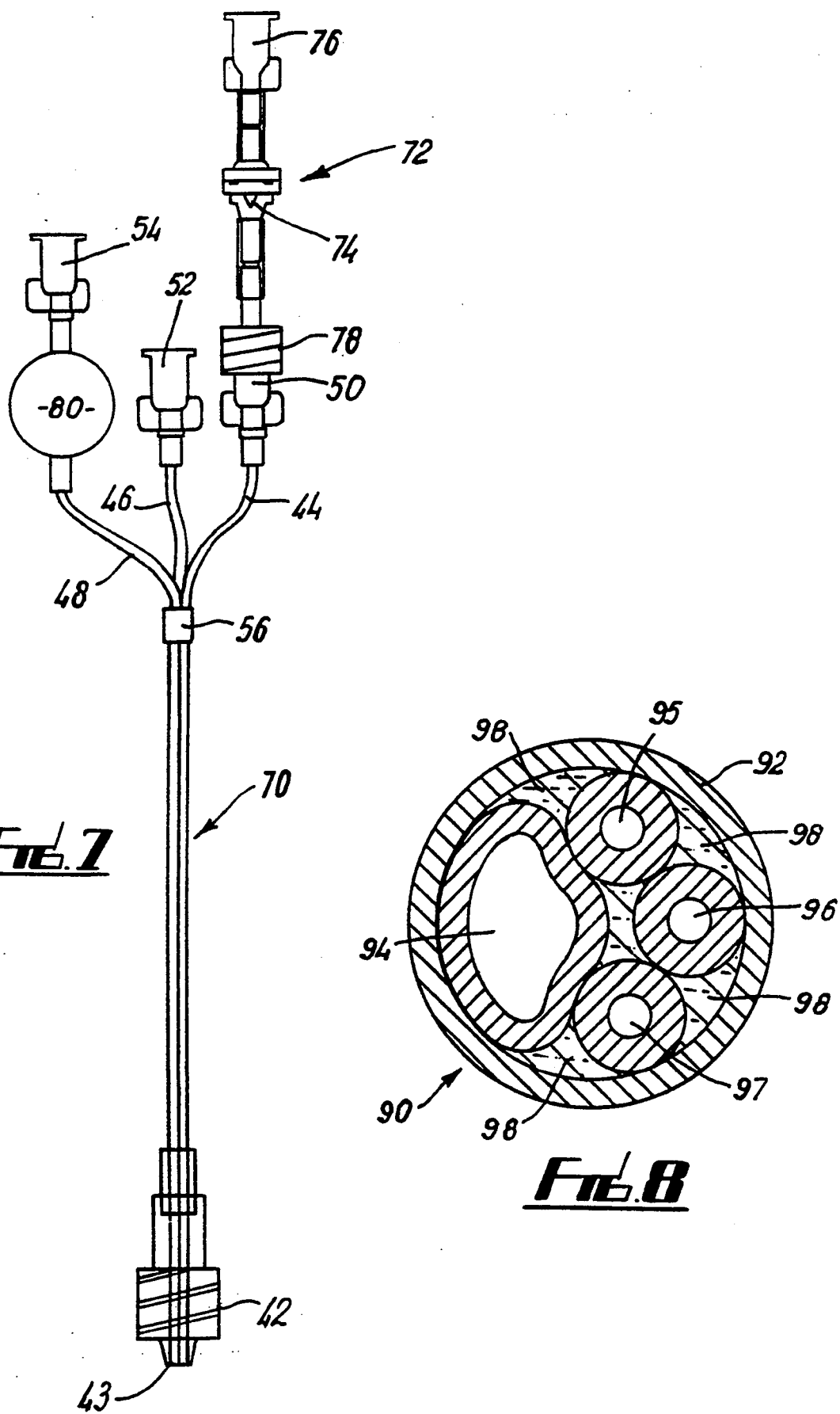

FLUID COUPLING AND THE METHOD OF MANUFACTURE

This invention relates to fluid couplings, and relates more particularly but not exclusively to couplings for joining several intravenous fluid conduits to a single intravenous cannula.

In the context of medical treatment of patients, it has become common practice to connect several tubes to a single intravenous cannula inserted into a vein of the patient, with the tubes each acting as a conduit, for a respective intravenous fluid. This practice allows the simultaneous supply to the patient of several intravenous fluids without multiple puncturing of the patient. For example, the patient may be continuously supplied with a saline solution, and intermittently injected with a drug, all through a single needle.

However, it has been found that conventional couplings cause unacceptable variations in flow rates of the different fluids. A drug meant to be delivered to the patient in a relatively short period of time may in fact be delivered over a long period, and at an unpredictable rate, or a fluid meant to be delivered at a slow rate over a long period of time may in fact be injected as a bolus (i.e. in one brief surge). Such unpredictable lack of control of fluid delivery rates has obvious dangers for the patient being injected.

The conventional couplings have the general shape of a "Y", and it is the volume of the downstream leg of the "Y" that is considered to account for the hazardous fluid delivery rate variations referred to above. It is an object of the present invention to provide a fluid coupling suitable for joining three or more intravenous fluid tubes to a single cannula, in which the internal volume otherwise giving rise to fluid delivery rate variations is substantially eliminated.

According to a first aspect of the present invention there is provided a fluid coupling for connecting a plurality of fluid sources to a single-bore outlet member, said coupling comprising a plurality of tubes mutually conjoined within a connector for attachment of said outlet member, each said tube extending through said connector to terminate at a point which is substantially contiguous with said outlet member when attached to said connector, the lumens of each said tube being mutually isolated by the tube walls until the termination of the tubes at said point, whereby in use of said fluid coupling with said single-bore outlet member connected thereto, fluid passing down any of said tubes discharges from the end of the respective tube substantially directly into the bore of said outlet member.

Said single-bore outlet member may comprise a cannula, which is preferably integral with or formed as a hypodermic trocar. Said outlet member preferably comprises the female half of a luer connector, and the connector of said coupling is preferably in the form of the matching male half of a luer connector.

The tubes of said coupling are preferably flexible tubes of a flexible polymeric material that is substantially unreactive with fluids conveyed thereby in use of the coupling. The end of each said tube remote from the connector of said coupling may be terminated by the female half of a respective luer connector.

Preferably a first tube is of short length and large bore, a second tube is of short length and fine bore, and a third tube is of variable length and of fine or medium bore. In this configuration the first tube provides a gravity feed line, the second tube is available for intermittent injection of fluid and the third tube, which is preferably made of, or lined with, a non-absorbent material, provides a line for supply of fluid from a pump. Further pump lines may be provided.

The large-bore first tube is preferably of 1.00–2.3 mm internal diameter and not more than 20 cm in length. This combination of large lumen and short length provides excellent flow rates on gravity feed.

The fine-bore tube or tubes are preferably of less than 0.8 mm, most preferably 0.2–0.5 mm, internal diameter; said second tube referred to above is preferably not more than 20 cm in length. Said third tube may be of short or long length.

The actual number of tubes in said coupling may be two, three, four, five or six, or some higher number.

One or more of the tubes of said coupling may incorporate an intermittent injection valve adjacent the upstream end thereof, and a bacterial filter intermediate said valve and the connector of said coupling, whereby bacteria and/or contaminating organisms that may be present in a pocket of fluid upstream of said valve are precluded from entering the patient in use of the coupling for intravenous injections.

Where the coupling is to be used for intravenous injections of fluids by means of one or more gravity feeds (each through a respective tube) and one or more pumped feeds (each through a respective tube), the coupling preferably incorporates a respective non-return valve in the or each tube carrying a gravity-fed fluid. The or each said non-return valve may be incorporated in the respective tube, or preferably formed as a separable fitting detachable from the respective tube.

According to a second aspect of the present invention there is provided a method of manufacturing a fluid coupling according to the first aspect of the present invention, said method comprising the steps of providing a connector having a single lumen, providing a plurality of tubes, passing each said tube through the lumen of said connector to project beyond the end of said lumen which will be substantially contiguous with said outlet member in use of said coupling, inserting packing material into said lumen of said connector to surround said tubes passing therethrough and to hold them in position relative to each other within the lumen, and severing the tubes where they project from said end of said lumen.

Said single-lumen connector is preferably formed as the male half of a luer connector. The end of each said tube remote from the single-lumen male luer connector half may have a respective female half of a luer connector secured thereto.

According to a third aspect of the present invention there is provided a method of manufacturing a fluid coupling according to the first aspect of the present invention, said method comprising the steps of providing a connector having a plurality of lumens equal to the number of tubes to be comprised in the finished coupling, providing a plurality of tubes, and connecting one said tube to a respective one of said lumens at the end thereof opposite the end which will be substantially contiguous with said outlet member in use of said coupling.

Said plural-lumen connector is preferably formed as the male half of a luer connector. The end of each said tube remote from the plural-lumen male luer connector half may have a respective female half of a luer connector secured thereto.

Embodiments of the invention will now be described by way of example with reference to the accompanying drawings wherein:

FIG. 4 is an overall representation of a first embodiment of intravenous fluid coupling of the present invention;

FIG. 5 is a section of part of the first embodiment of FIG. 4, to an enlarged scale;

FIG. 6 is a transverse section of the part shown in FIG. 5, taken on the line VI—VI in FIG. 5;

FIG. 7 is an overall representation of a second embodiment of intravenous fluid coupling of the present invention; and FIG. 8 is a transverse cross-section of part of a third embodiment of fluid coupling of the present invention.

Figure 1:
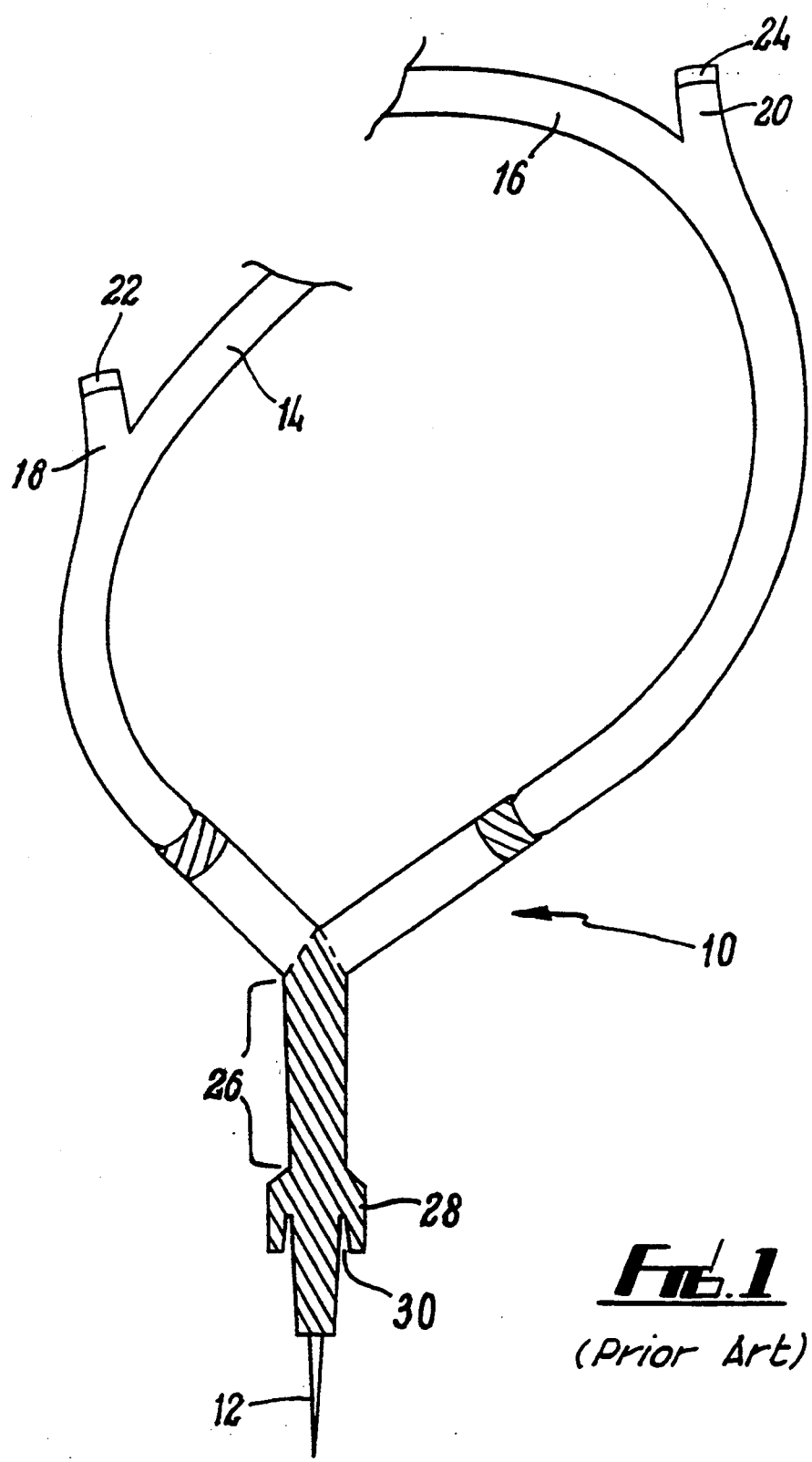
FIG. 1 is a schematic representation of a prior-art intravenous fluid coupling.

Referring first to FIG. 1, this drawing schematically illustrates a conventional prior-art intravenous fluid coupling 10 for administering a patient (not shown) with intravenous fluids from two sources through a single cannula or hypodermic needle 12. The coupling 10 comprises two tubes 14 and 16 whose upstream ends (not shown) are coupled to gravity-feed fluid bags (not shown) or to infusion pump sets (not shown). A respective short side branch 18 and 20 in each tube 14 and 16 is capped with a respective rubber cap or bung 22 and 24 to enable intermittent injections, e.g. of drugs.

Figure 2:
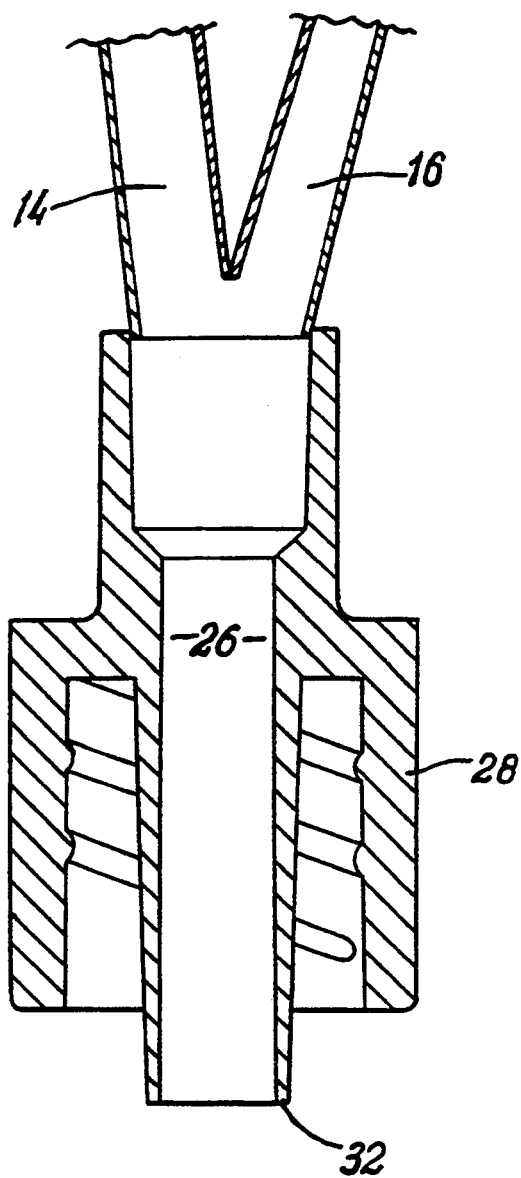
FIG. 2 is a section of part of the prior-art coupling of FIG. 1, to an enlarged scale.

The prior-art coupling 10 is of a kind sometimes termed a "Y-set" from considerations of geometric analogy, i.e. the two tubes 14 and 16 merge into a common descending leg 26 which connects through a luer connector 28 (male half) and 30 (female half) to the cannula 12. This is shown to an enlarged scale in FIG. 2, where the cannula 12 and its integral female luer connector half 30 is detached for clarity. Clearly, the internal volume of the common descending leg 26 of the Y-set is substantial in relation to the volume of a comparable length of either of the tubes 14 or 16, and much greater than the internal volume of a typical cannula. It is significant to note that the relatively narrow-bore cannula 12 will directly abut or be substantially contiguous to the lower or downstream end 32 of the male luer connector half 28 when the coupling 10 is in use.

Figure 3:
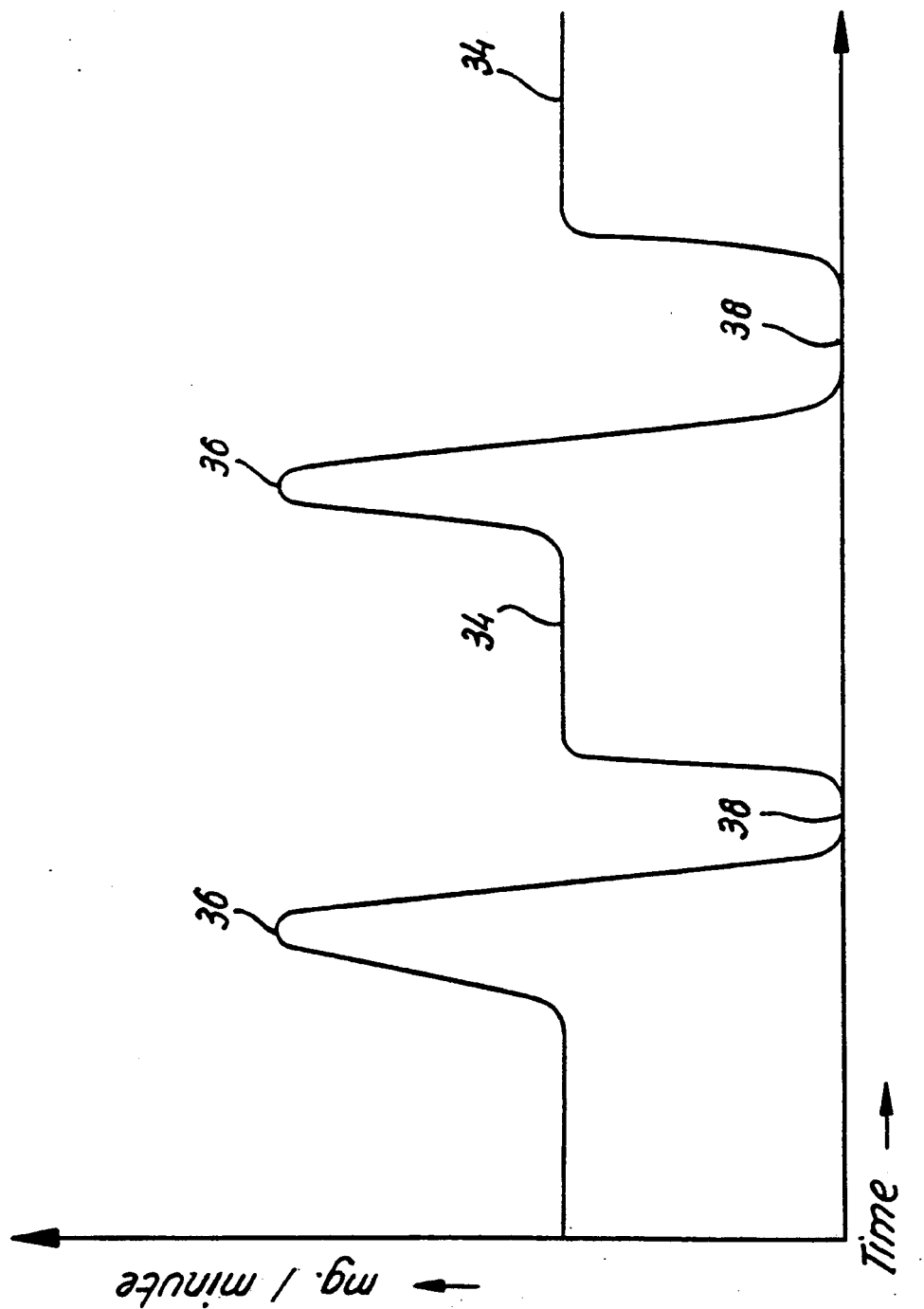
FIG. 3 is a flow rate/time chart of operation of the prior-art coupling of FIG. 1.

The volume of the common leg 26 intervening between the individual fluid lines 14 and 16, and the cannula 12, allows uncontrolled mixing of the various fluids and drugs intended to be administered to the patient. For example, in commercial Y-sets, this common volume is usually greater than 0.5 milliliters. Thus, when one intravenous fluid is being metered down one of the tubes 14 at a rate of 0.5 milliliters per hour, an injection through the bung 24 into the side branch 20 of the other tube 16 could deliver a bolus (surge) of at least one hour's worth of the fluid being slowly infused down the first tube 14. Following this large bolus, a delay of up to one hour could elapse prior to resumption of infusion of the first fluid, while the common leg 26 refilled with the first fluid through the tube 14. This gross malfunction of intended patient infusion is schematically illustrated in FIG. 3, which is a graph of infusion rate (vertical axis; flow rate of milligrams per hour to an arbitrary linear scale) versus time (horizontal axis; units of time to an arbitrary linear scale). In FIG. 3, reference 34 represents the intended fusion rate of intravenous fluid through the tube 14, reference 36 represents the bolus or surge of this fluid due to an injection into the other tube 16, and reference 38 denotes the following trough of virtually total starvation of the fluid while the common leg 26 refills. Because the fluid injected into the tube 16 (typically a drug) displaces the steadily infused fluid from the tube 14 to at least partially fill the common leg 26, the actual dosage rate to the patient of fluid injected into the tube 16 is not controlled, and may be less than intended. FIG. 3 shows two such uncontrolled variations in the patient's dosage rates, and clearly illustrates the potential dangers to the patient.

The present invention comprises a new form of fluid coupling, suitable for use in supplying several intravenous fluids to a patient through a single cannula, and which largely eliminates the above-described hazard.

Referring now to FIGS. 4, 5 and 6, these illustrate a first embodiment 40 of fluid coupling in accordance with the invention. FIG. 4 is an overall view of the first embodiment, FIG. 5 is a detail sectional view of the lower end of the first embodiment, to an enlarged scale (and corresponding to the FIG. 2 view of the prior art), and FIG. 6 is a transverse section of the first embodiment, taken on the line VI—VI in FIG. 5.

The first embodiment 40 (FIG. 4) comprises a male luer connector half 42 to which are secured a short, relatively large-bore and two relatively fine-bore flexible intravenous-fluid-carrying tubes 44, 46, and 48. A respective female luer connector half 50, 52 and 54 terminates the upstream end of the tubes 44, 46 and 48 (i.e. the tube ends remote from the connector 42) to facilitate the attachment of respective sources of intravenous fluid (not shown), e.g. gravity-feed bags and/or motorized infusion pumps. A movable collar or tubing grip 56 can be slid along the tubes 44, 46 and 48 to selectively vary the length of tubing up to the connector 42 that is clustered as a compact group, and to selectively vary the potential maximum mutual separation of the connectors 50, 52 and 54 to suit the locations of the fluid sources.

The tube 44 is less than 20 cm in length, in this particular embodiment 15 cm, and 1.5 mm in internal diameter, and in use is connected to a gravity-feed saline supply. The tube 46 is also 15 cm in length but is of 0.5 mm internal diameter; this tube 46 in use has a sealed upstream end through which intermittent injections can be made for supply to the patient along the tube 46. The tube 48 in this embodiment is also 15 cm in length and of 0.5 mm internal diameter, and in use is connected through its upstream end to a drug supply from a motorized infusion pump.

The lower (downstream or outlet) end of the first embodiment 40 in the vicinity of the connector 42 is shown in section and to a much-enlarged scale in FIG. 5. This part of the coupling 40 comprises a conventional single-lumen male luer connector half 42 to which are secured the downstream or outlet ends of the three tubes 44, 46 and 48 by being embedded within the lumen by a solidified adhesive or resin 58 (see particularly the transverse cross-section illustrated in FIG. 6). The lumen of the connector 42 may have an internal diameter of about 0.125 inches (3.2 millimeters).

This part of the coupling 40 is conveniently manufactured by the steps of providing a conventional single-lumen male luer connector half, providing the three intravenous fluid tubes and threading the tubes downwards through the male connector (i.e. with the connector aligned as shown in FIG. 5) until the tubes project from the end 43 of the male connector 42 which will be contiguous with a cannula when connected thereto by a corresponding female luer connector half. Thereupon the tubes 44, 46, and 48 are secured within the connector lumen 42 by at least partially filling the connector lumen 42 around the tubes 44, 46, and 48 with a suitable adhesive or resin 58 so as to embed the tubes 44, 46, and 48 within the connector lumen 42. Then, when the adhesive or resin 58 has cured, the projecting tube ends and any overflowed adhesive or resin are severed at the end 43 of the connector 42, e.g. by slicing them with a sharp scalpel or other suitable cutting tool, to leave a flush connector end 43 in which the three tubes 44, 46, and 48 are solidly embedded, the so-fabricated coupling end 43 being penetrated only by the lumens of the tubes, as depicted in FIG. 6.

Thereby, the resultant coupling 40 can have a cannula (not shown) having a female luer connector half integral therewith or secured thereto, connected to the connector 42 of the coupling 40 such that the embedded tube ends are substantially contiguous with the bore of the so-connected cannula. This arrangement results in a zero or minimal common intravenous fluid volume between the downstream ends of the individual intravenous fluid carrying tubes 44, 46 and 48, and the cannula through which the fluids are conjointly delivered into the patient. Thus the potentially dangerous disadvantage of the prior art couplings, described above with reference to FIGS. 1–3, is substantially obviated. Compared to the prior art "Y-sets" the present invention could analogously be termed a "V-set" due to the absence therefrom of a common descending limb proceeding from the conjunction of the two incoming "arms" of source-connecting tubing.

FIG. 7 illustrates a second embodiment 70 of fluid coupling in accordance with the invention, and which is based on the first embodiment 40 (FIG. 4). Accordingly those parts of the second embodiment 70 which are structurally and functionally equivalent to corresponding parts of the first embodiment 40 are given the same reference numerals as were employed in the description of the first embodiment. The following description of the second embodiment 70 will concentrate on those parts which differ from the first embodiment 40, and for a description of any part of the second embodiment 70 not detailed below, reference should be made to the foregoing description of the relevant part of the first embodiment 40.

In the second embodiment 70, the tube 44 is provided with a non-return valve set 72 comprising an in-line non-return valve 74 coupled between a female luer connector half 76 for attachment to a gravity-feed intravenous fluid source (not shown), and a male luer connector half 78 for attachment to the female luer connector half 50 terminating the upstream end of the tube 44. The non-return valve set 72 serves to provide an anti-reflux function which prevents reverse flow of fluid into the gravity-feed intravenous fluid source via the tube 44 in the event of a pressure surge in one of the other tubes 46 or 48 as may be occasioned, for example, by the intermittent operation of a motorised infusion pump acting as the intravenous fluid source for that other tube.

While the non-return valve set 72 is preferably detachable from the remainder of the coupling 70 as shown in FIG. 7, the non-return valve set 72 may also be formed integral therewith (e.g. by eliminating the connectors 50 and 78, and by directly connecting the outlet or downstream side of the non-return valve 74 directly to the upstream end of the tube 44).

The second embodiment 70 is further modified in comparison to the first embodiment 40 by the provision of an in-line bacterial filter 80 connected into the tube 48 immediately downstream of the respective female luer connector half 54. The filter 80 may be a flat disciform filter as schematically depicted in FIG. 7, or any other suitable shape. The filter 80 serves to prevent contaminating organisms upstream thereof, e.g. in the connector 50, from reaching the patient.

The non-return valve set 72 and the in-line bacterial filter 80 can be employed in any suitable numbers (one per tube) according to requirements, and independently of each other.

While the first and second embodiments (40, FIG. 4; 70, FIG. 7) have been illustrated by way of example as employing three tubes to individually couple three intravenous fluid sources to a patient via a single cannula, a fluid coupling in accordance with the invention may have more than three tubes for coupling up to a correspondingly greater number of intravenous fluid sources through a single cannula (or any other suitable outlet member). By way of non-limiting examples, a fluid coupling in accordance with the invention may have four, five, six or more, up to twelve or more tubes secured into a single outlet connector. In each such instance, the appropriate number of tubes may be secured inside the lumen of a single-lumen connector (e.g. as described in respect of the first embodiment 40), or each such tube may be secured to the respective lumen of a plural-lumen connector having a number of lumens (three, four, five, six, or more up to twelve or more) equal to the requisite number of tubes to be secured to the plural-lumen connector.

As an example of such a multi-tube connection, FIG. 8 is a transverse cross-section of a third embodiment 90 of a fluid coupling in accordance with the present invention, in which four tubes are embedded in a single-lumen connector.

FIG. 8 corresponds to the sectional view of the first embodiment shown in FIG. 6 but to a somewhat larger scale. In FIG. 8, the third embodiment 90 comprises a male luer connector half 92 holding four intravenous fluid supply tubes 94, 95, 96 and 97 together embedded in a suitable adhesive or resin 98. As will be seen from the drawing, the tube 94 is of considerably greater lumen diameter than the tubes 95, 96 and 97.

Advantages of the present invention over the prior art will now be discussed in greater detail, in the context of use of the fluid coupling for supplying intravenous fluids to a patient through a single cannula.

The advantages of the invention ("V-sets") over the previous designs of fittings ("Y-sets") include the following:

1. The new V-set reduces the risk of drug surges and dips (sudden rises and troughs in the prescribed infusion rate).
2. Intermittent injections to the cannula can be made direct to the cannula, with no drug mixing with any of the intravenous solutions in the other lines prior to the cannula. Hitherto, this has not been possible to achieve with conventional fittings available. Injections have had to be made into an infusion line which provides access to the cannula.
3. The risk of phlebitis, septicaemia and needle stick injuries had been reduced by a unique arrangement of a valve system and a filter in a low volume line which provides direct access to the intravenous cannula.

4. Previous attempts to minimize dead space have been associated with the use of fine bore tubing, which has usually been relatively long. The use of at least one large bore, short length, flexible tube allows rapid gravity flow to be associated with smaller infusion lines through the same fitting. This provides the combined benefits of a high flow rate on one line, together with no dead space within the fitting.

Advantages of the design features to reduce the risk of drug surges and troughs:

The risk of drug surges is reduced by eliminating the common limb of a Y fitting in the same way that a V has no common limb. This descending section of the Y (common limb) in commercial fittings varies between 0.5 milliliters and 10.0 milliliters. The 0.5 milliliters versions have the advantage of having a relatively small volume but the disadvantage that they are clumsy fittings on the posterior aspect of the arm and that they cross over the wrist .and expose the vein to stresses when the wrist is flexed or extended. It is common therefore to have a flexible, common limb connected to the cannula and turned around in the U shape. It is not uncommon for this limb to be 1 to 10 milliliters in volume. With the growth of accurate small infusion pumps, many of which use 10 milliliter syringes over a 24-hour period, the common space in the descending limb of the Y fittings has become more and more significant. In many situations this common space contains 1 to 5 hours worth of drug to be infused, which means the patient will not receive any drug for 1-5 hours (trough). Intermittent injections through another limb of the fitting exposes the patient to the risk that the limb may be flushed through suddenly with the resultant effect that the constant-rate-infusion fluid is delivered at extremely high rates for short periods of time (surge).

During the course of drug infusion, surges can also occur when an infusion pump delivers drug into a gravity-fed line. The pressure generated by most pumps will exceed the pressure in the gravity-fed line and on occasions when the cannula is partially blocked fluid will travel from the high pressure line to the low pressure line. The cannula can become blocked with flexion of the wrist and use of the arm for measurement of blood pressure. The new coupling has incorporated detachable anti-reflux valves which can be added to any number of gravity-fed lines to prevent a single pump-driven line accidentally filling them. Until this time, these anti-reflux valves have been fixed to devices with intravenous lines and have not been detachable. To make them detachable allows a flexible system that can be changed as gravity-fed or pump-fed lines are added.

Advantages of the design feature to provide direct access from an intermittent injection site to the cannula without any mixing in the intravenous lines:

The V-set arrangement allows for as many lines as might be required having direct access to the cannula with no region of mixing prior to fluid entering the cannula. The commonest design that will be useful will allow two intravenous lines with one intermittent injection line for a three-line V-set. Some sets may have up to 12 separate intravenous pump lines, with one of these dedicated to intermittent injections. In the past injections made through a rubber bung or a valve arrangement into an intravenous line always have the risks of the drug mixing with other drugs in the line, and lodgement in the line without ever reaching the patient. This new design specifically prevents this from happening as each of the gravity lines can have an anti-reflux valve preventing fluid being pushed back up the gravity lines. A guarantee therefore exists for quality assurance with intermittent injections which has not previously existed. All 2 milliliters injected through the rubber bung or the valve arrangement on the intermittent injection line will reach the patient except for the dead space in the cannula and the remaining dead space in the line. In most cases the cannula dead space will be 0.02 milliliters and it is not difficult to keep the dead space in line below 0.15 milliliters. The design features therefore guarantees that the majority of a 2 milliliter injection will arrive specifically at the patient, without the risk of it being lost in intravenous line dead space. Frequently, with current arrangements, a small injection such as 2 milliliters will be delivered through a rubber bung in one of several lines connected to a Y-set arrangement. If the nursing staff are not careful the drug may be added to a line which might not be running with the risk that it never reaches the patient. The design of the coupling of the present invention and the practice of using the intermittent injection line for all injections provides quality assurance where known quantities of drugs will always be delivered to the patient. This feature has not previously been available. It could only previously be achieved with flushing.

Advantages of the design features to reduce the risk of needle stick injuries, the risk of septicaemia and the risk of thrombo-phlebitis:

Intermittent injection sites of intravenous lines are traditionally rubber bungs which are cleaned with alcohol prior to injecting fluid into the intravenous line. A number of valve arrangements where the valve sits low inside a female luer lock system have been introduced to the market but these have had significant disadvantages. There is usually a pocket of fluid which exists above the valve with a risk that this pocket of fluid becomes significantly contaminated with organisms. As this pocket of fluid sits in a recess within the housing of a female luer lock fitting it is impossible to clean it with an alcohol swab prior to use. For this reason a variety of valve arrangements which have been useful for short term venous access during anaesthesia have been unpopular on intravenous lines. By careful arrangement of an intermittent injection valve, followed by a filter arrangement to exclude organisms on the intermittent injection line, it is possible to create a specific valve filter infusion line with a direct access to a cannula by-passing the other intravenous lines. This arrangement gives the following benefits:

the valve arrangement which would previously be safe to use for only very short periods of time can be used for long periods of time because any bacteria that may be present within the valve arrangement are filtered out prior to entry to the patient-supplying line. This valve filter arrangement is the only way such valves should be allowed to be placed on intravenous lines. Without this valve filter arrangement the valve would have a high risk of introducing organisms to intravenous lines and would therefore be unsafe. This arrangement therefore overcomes the deficiency of the valves which have significant dead space and residual organisms which previously precluded their use from intravenous lines.

The arrangement of the valve and filter provides a fitting which allows the addition of a number of intravenous lines where all intermittent injections will be through a valve filter arrangement. The valve filter arrangement provides protection for the intravenous lines so that organisms will not be injected and where poorly dissolved antibiotics will not be injected. The risk of thrombo-phlebitis and septicaemia will therefore be reduced by the risk of this unique V-set arrangement.

The following specific advantages arise from the design of the V-sets in accordance with the invention:

1. Y-sets and 3 way taps involve several intravenous lines meeting through a common limb. V-sets provide direct access to the cannula for each of the intravenous lines without any mixing prior to the cannula.
2. The V-sets provide an intermittent injection line with direct access to the cannula with no mixing between the intermittent line and continuous flow lines or in fact mixing of any of the flow lines.
3. The intermittent injection line can have a minimum dead space by having an extremely fine lumen. This can be well below 0.1 milliliter which is below the dead space in most commercial systems which is virtually always above 1 milliliter.
4. The use of a valve arrangement on the intermittent line in series with a filter provides a system which eliminates the use of needles on intravenous lines. The elimination of this use of needles saves costs with needles, and also eliminates the risk of needle stick injuries.

While certain modifications and variations have been described above, the invention is not restricted thereto, and other modifications and variations can be adopted without departing from the scope of the invention as defined in the appended claims.

What is claimed is:

1. A method of manufacturing a fluid coupling for connecting a plurality of fluid sources to a cannula, said method comprising the steps of:
    providing a connector having a single lumen,
    providing at least three tubes wherein at least one of said tubes is of a relatively large bore size as compared with at least one of said remaining tubes,
    passing each said tube through the lumen of said connector to project beyond the end of said lumen, which will be substantially adjacent to said cannula in use of said coupling, the bore of each said tube being mutually isolated by the tube walls until the termination of the tubes,
    inserting adhesive or resin into said lumen of said connector to surround said tubes passing therethrough, and
    when said adhesive or resin has substantially cured, severing said tubes and any overflowed adhesive or resin where they project from said end of said lumen whereby, in use of said fluid coupling with said cannula connected thereto, fluid passing down any of said tubes discharges from the end of said respective tube substantially directly into the bore of said cannula.

2. A method as claimed in claim 1, wherein said single-lumen connector is formed as the male half of a luer connector.

3. A method as claimed in claim 2, wherein the end of each said tube remote from the single-lumen male luer connector half has a respective female half of a luer connector secured thereto.

* * * * *